(12) United States Patent
Towns et al.

(10) Patent No.: US 9,380,835 B2
(45) Date of Patent: Jul. 5, 2016

(54) FOOTGAUGE

(75) Inventors: Chris Towns, Taunton (GB); Peter Rickett, Englefield Green (GB); Dan Innes, London (GB); Yaan Kinally, Middlesex (GB)

(73) Assignee: C. & J. CLARK INTERNATIONAL LIMITED, Street, Somerset (GB)

( * ) Notice: Subject to any disclaimer, the term of this patent is extended or adjusted under 35 U.S.C. 154(b) by 106 days.

(21) Appl. No.: 14/234,962

(22) PCT Filed: Jul. 10, 2012

(86) PCT No.: PCT/GB2012/051626
§ 371 (c)(1),
(2), (4) Date: Mar. 5, 2014

(87) PCT Pub. No.: WO2013/014422
PCT Pub. Date: Jan. 31, 2013

(65) Prior Publication Data
US 2014/0182152 A1    Jul. 3, 2014

(30) Foreign Application Priority Data

Jul. 25, 2011 (GB) .................................. 1112695.0
Dec. 22, 2011 (GB) .................................. 1122100.9

(51) Int. Cl.
*A43D 1/02* (2006.01)
*A61B 5/107* (2006.01)
*G06F 1/16* (2006.01)

(52) U.S. Cl.
CPC *A43D 1/02* (2013.01); *A43D 1/025* (2013.01); *A43D 1/027* (2013.01); *A61B 5/1074* (2013.01); *G06F 1/1632* (2013.01)

(58) Field of Classification Search
CPC .......... A43D 1/02; A43D 1/027; A61B 5/1074
USPC ....................................................... 33/3 A, 512
See application file for complete search history.

(56) References Cited

U.S. PATENT DOCUMENTS 2,175,116 A * 10/1939 Hack et al. ........................ 33/3 B
2,601,131 A *  6/1952 Weber ............................. 33/3 A (Continued)

FOREIGN PATENT DOCUMENTS

| JP | 49-038458 U | 4/1974 |
| JP | 03-109003 A | 5/1991 |
| JP | 2004-310196 A | 11/2004 |

OTHER PUBLICATIONS

International Search Report and Written Opinion of the International Searing Authority Application No. PCT/GB2012/051626 Completed: Nov. 13, 2012; Mailing Date: Nov. 22, 2012 8 pages.

(Continued)

*Primary Examiner* — Christopher Fulton
(74) *Attorney, Agent, or Firm* — Squire Patton Boggs (US) LLP

(57) ABSTRACT

A footgauge having a foot support plate having an upper surface on which the foot is placed with the heel against a fixed heel abutment. A touchscreen computer device (TCD) is inserted in a tray below the surface and engages a movable toe abutment. The toe abutment is moved into engagement with the foot and the user then and the user then presses a fixed pointer into contact with the screen of the TCD. The TCD is programmed and calibrated so as to give a foot length reading which is dependent on how far the toe abutment is moved towards the heel abutment.

19 Claims, 16 Drawing Sheets

(56) References Cited

U.S. PATENT DOCUMENTS

| | | | |
|---|---|---|---|
| 3,579,837 A | | 5/1971 | Soriano |
| 3,834,029 A | * | 9/1974 | Stiebel ............................ 33/3 C |
| 4,807,368 A | * | 2/1989 | Beyl ................................ 33/3 B |
| 4,932,852 A | * | 6/1990 | Suzuki .............................. 425/2 |
| 5,128,880 A | * | 7/1992 | White ............................ 382/165 |
| 5,156,161 A | * | 10/1992 | Lollar ............................ 600/587 |
| 5,164,793 A | * | 11/1992 | Wolfersberger et al. ...... 356/607 |
| 5,539,677 A | | 7/1996 | Smith |
| 5,729,905 A | | 3/1998 | Mathiasmeier et al. |
| 5,822,223 A | * | 10/1998 | Genest .......................... 702/155 |
| 6,205,230 B1 | * | 3/2001 | Sundman et al. ............. 382/100 |
| 6,834,437 B1 | | 12/2004 | Kilgore et al. |
| 2003/0033723 A1 | * | 2/2003 | Snook ............................ 33/515 |
| 2013/0167391 A1 | * | 7/2013 | Pratinidhi et al. ............. 33/512 |

OTHER PUBLICATIONS

Saudi Arabian Patent Office, Saudi Arabian Office Action for corresponding Saudi Arabian Patent Application No. 112330710, dated Jun. 30, 2015.

Japanese Patent Office, Office Action for corresponding JP Patent Appln. No. 2014-522148, May 6, 2016.

* cited by examiner

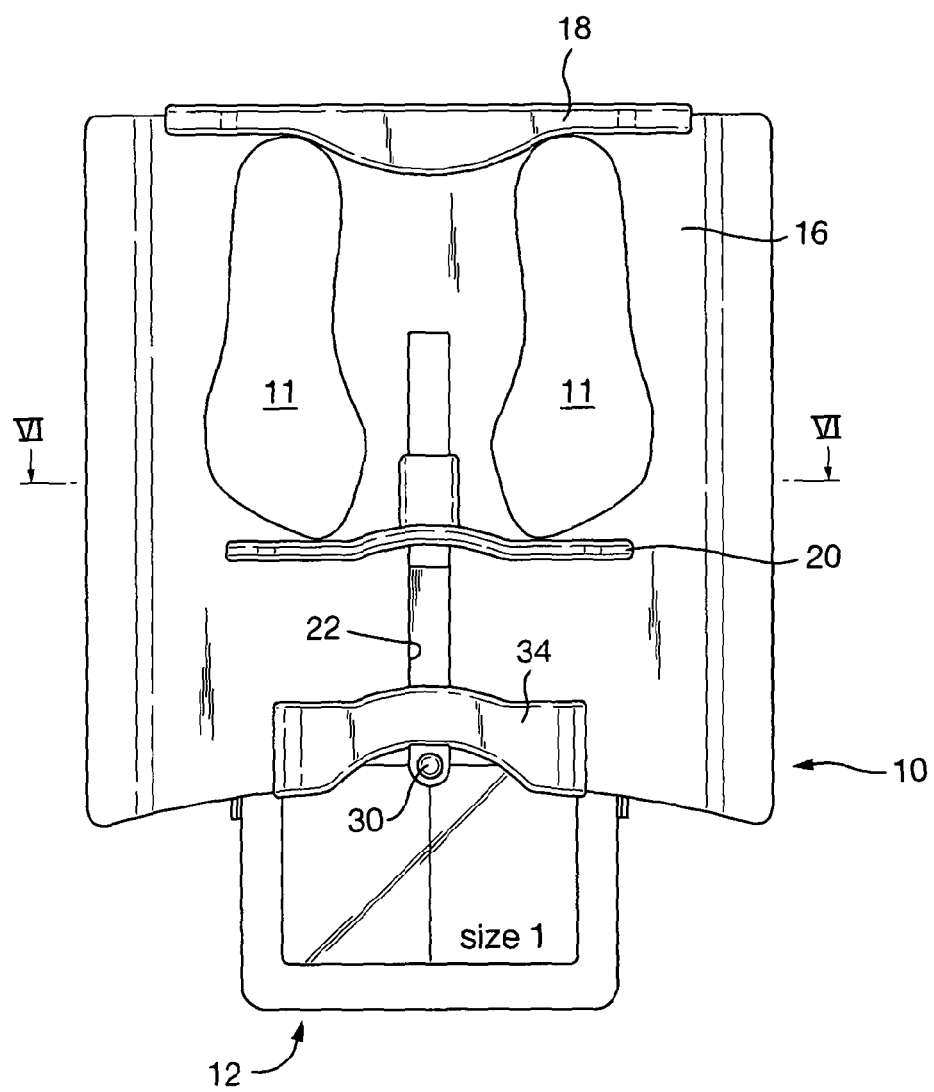

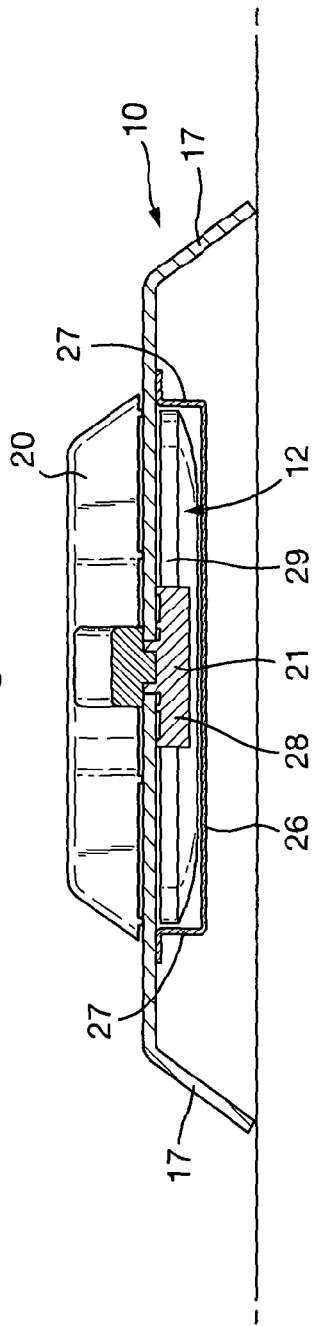
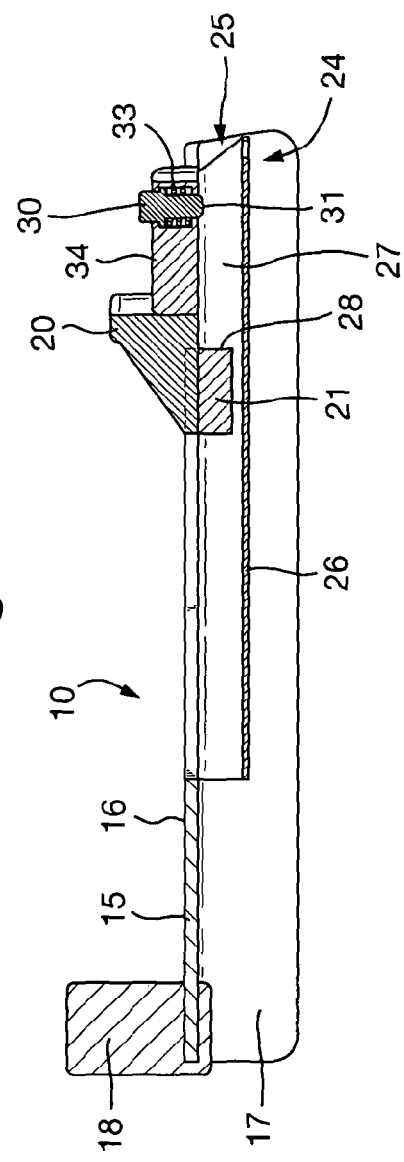

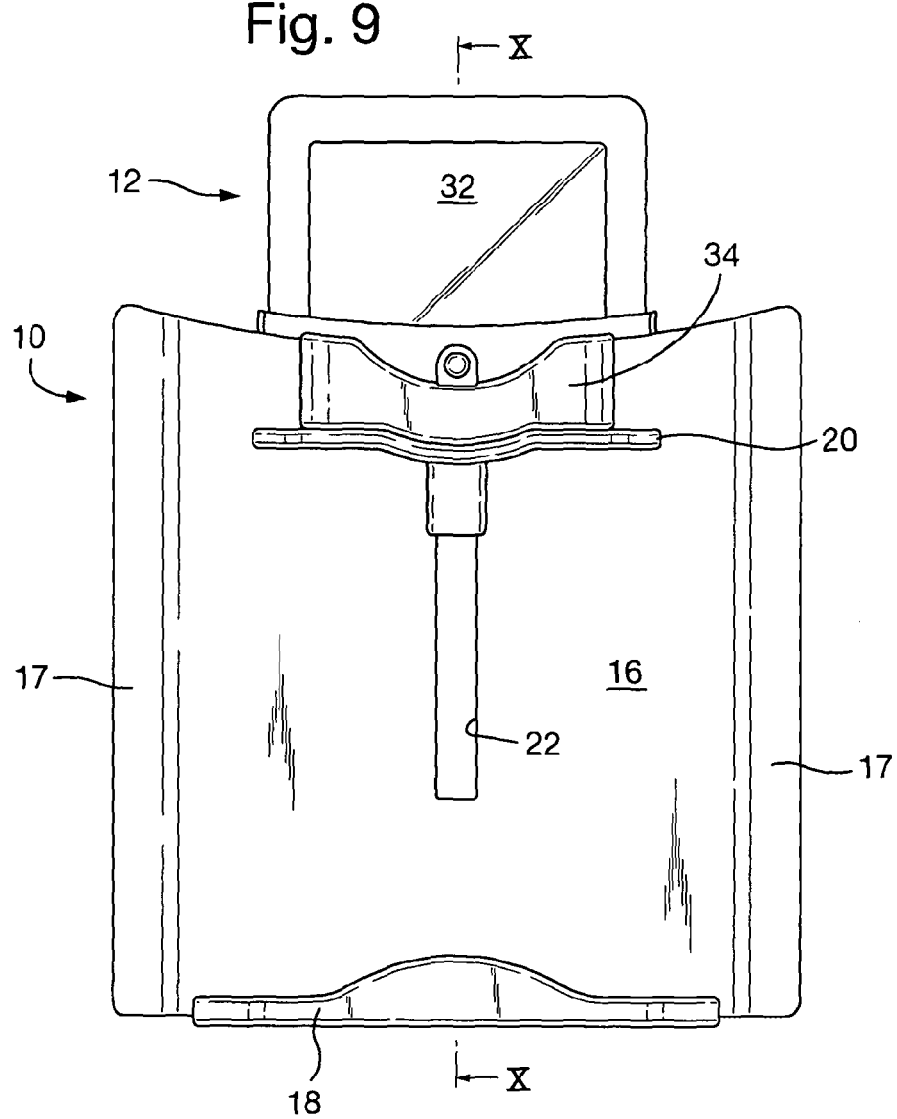
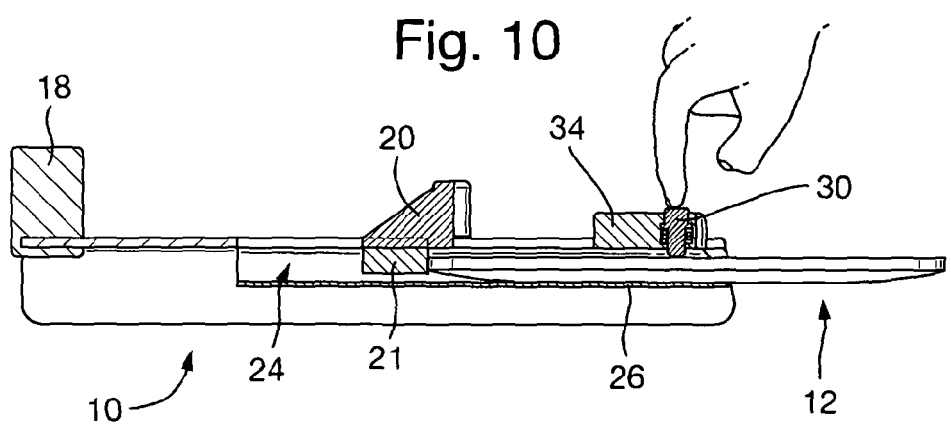

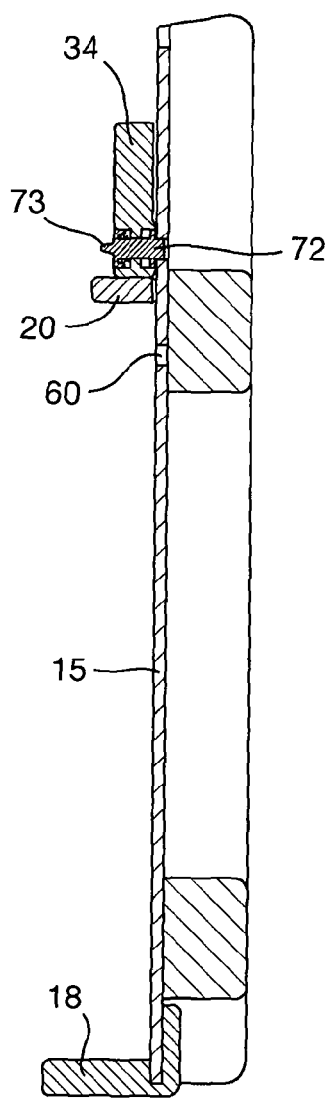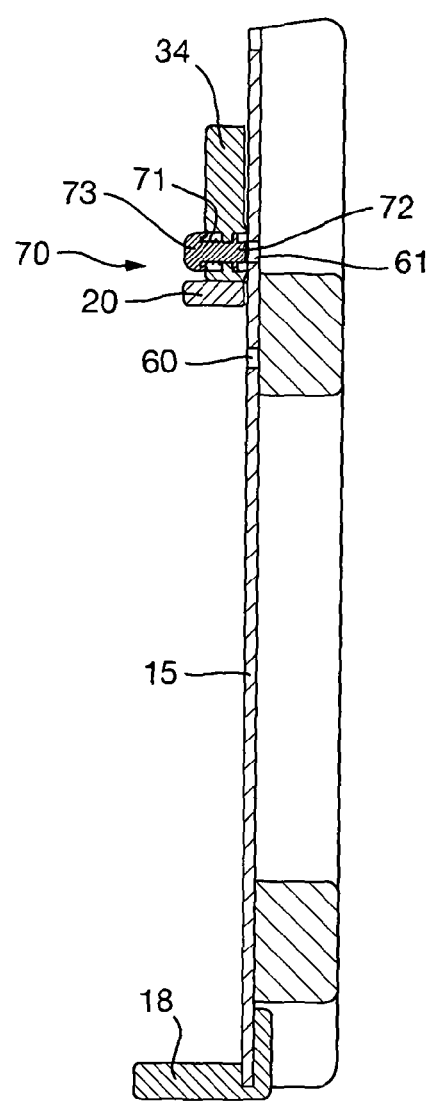

FOOTGAUGE

FIELD OF THE INVENTION

The present invention relates to footgauges for measuring the length of a foot, particularly but not exclusively for the purpose of determining the correct size of footwear. The footgauges can be used to measure feet, irrespective of gender or age.

BACKGROUND OF THE INVENTION

Many types of footgauge are known for foot length measurement. These range from simple and portable manually operated devices which indicate a particular shoe size on a printed scale to complex fixed location devices having a display screen and motorised foot engagement plates. These known devices operate effectively but do not address all issues regarding portability and product availability.

SUMMARY OF THE INVENTION

According to a first aspect of the present invention, there is provided a footgauge for measuring the length of a foot, the footgauge comprising:
- (i) a foot support having a foot support plate on which the underside of the foot is placed;
- (ii) a heel abutment for engaging the heel of the foot;
- (iii) a toe abutment for engaging the foremost extremity of the foot;
- (iv) means for receiving a touchscreen computer device;
- (v) contact means for enabling the screen of the touchscreen computer device to be contacted to indicate the length of the foot;
  wherein the heel abutment and the toe abutment are movable relative to each other.

In preferred arrangements, the heel abutment is fixed relative to the foot support and the toe abutment is movable in a linear lengthwise direction towards or away from the heel abutment and ideally the toe abutment is resiliently biased into a position remote from the heel abutment.

With some embodiments, the toe abutment has a downward projection which projects through a guide slot in the foot support plate, the guide slot extending in said linear lengthwise direction. Conveniently, the receiving means for the touchscreen computer device comprises a support tray below the foot support plate, the width of the support tray enabling in use the touchscreen computer device to be slidably moved in said linear lengthwise direction with the plane of the screen being parallel with the general plane of the foot support plate and the support tray being open at its forward end for receiving the touchscreen computer device.

Preferably, the downward projection of the toe abutment extends downwardly into the support tray so as to be engaged in use by the rear end of the touchscreen computer device, rearward movement of the touchscreen computer device moving the toe abutment rearwardly into engagement with the foot.

Usually, the foot support plate is adapted to receive a pair of feet, the heel abutment is dimensioned to engage both heels and the toe abutment is dimensioned to engage the forwardmost extremity of one or both feet and normally the slot is positioned so as to be centrally positioned between the two feet when the footgauge is in use.

It is a preferred embodiment that said contact means comprises a movable pointer which is provided in a fixed location relative to the foot support and which is resiliently biased away from the touchscreen computer device when in use but is selectively movable into engagement with the screen of the touchscreen computer device. In some arrangements the pointer is provided on a forward section which is movable between, and securable in, a number of fixed locations relative to the foot support. Preferably the forward section is securable by means of one or more buttons having a push down/twist bayonet mechanism engaging in cooperating holes in the foot support.

Preferably, the foot support includes downwardly extending support elements for engaging a floor.

According to a second aspect of the present invention, there is provided a footgauge arrangement comprising a footgauge as described above in conjunction with a touchscreen computer device.

In some arrangements, the touchscreen computer device is removable from the receiving means. Ideally, the touchscreen computer device is programmed to give a foot length indication when the screen is contacted and preferably the touchscreen computer device is programmed to indicate footwear availability for a foot length indication.

BRIEF DESCRIPTION OF THE DRAWINGS

Embodiments of the present invention will now be described in more detail. The description makes reference to the accompanying drawings in which:

FIG. 5 is a plan view of the FIG. 1 footgauge arrangement displaying a shoe size, FIG. 6 is a lateral cross-section on line VI-VI of FIG. 5 but omitting the feet being measured, FIG. 8 is a lengthwise cross-section on line VIII-VIII of the footgauge of FIG. 7, FIG. 9 is a plan view of the footgauge arrangement of FIG. 1 in use but omitting the feet being measured, FIG. 10 is a lengthwise section on line X-X of the footgauge arrangement shown in FIG. 9, FIG. 12 is a sectional view on line AA of FIG. 11, FIG. 14 is a sectional view on line AA of FIG. 13.

DETAILED DESCRIPTION OF THE INVENTION

Figure 1:
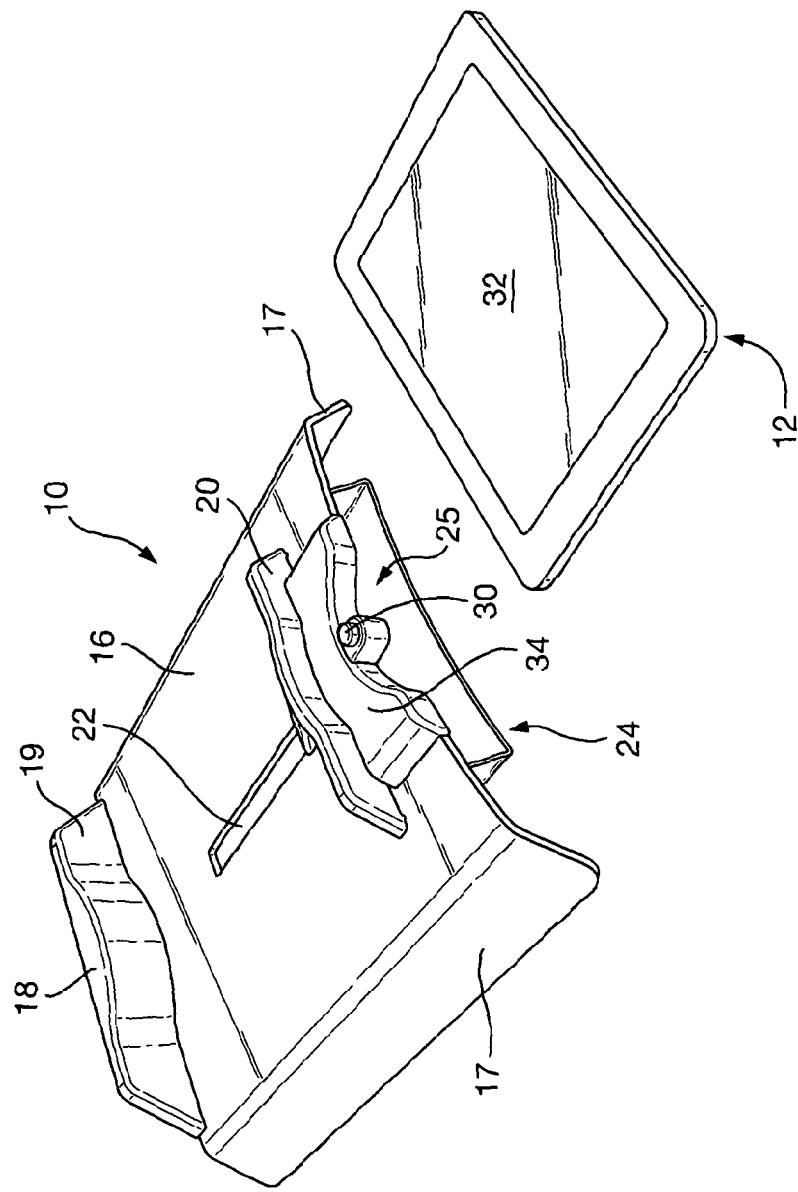
FIG. 1 is a perspective view of a footgauge arrangement comprising a footgauge according to the present invention together with a touchscreen computer device.

In FIGS. 1 to 10 there is shown a footgauge 10 for use in measuring the length of feet 11. Although the footgauge 10 is shown as being for measuring a pair of feet 11 together it is readily possible for the footgauge to be modified for measuring single feet individually. The footgauge 10 is to be used with a touchscreen computer device (TCD) 12, for example an IPad (Registered Trademark of IP Application Development LLC and/or Apple, Inc.) device. Such TCDs can be readily programmed so as to constitute with the footgauge an effective footgauge arrangement for measuring feet 11.

The footgauge 10 comprises a foot support plate 15 having an upper surface 16 on which the undersides of the feet 11 are placed. The foot support plate 15 has at each of its two oppositely disposed lateral edges a downwardly extending support element 17, in this case angled, which engage the floor or other support surface (not shown) such that the support plate 15 is somewhat raised. Alternative support elements could, of course, be used such as a simple leg at each corner.

At the rear of the foot support plate 15 is an upstanding heel abutment 18 which in this embodiment has a slightly contoured forward facing surface 19. The heels of the feet 11 engage the heel abutment 18 and the surface 19 is ideally anatomically contoured so as to encourage correct positioning of the feet on the support plate 15.

Towards the forward end of the foot support plate 15 is an upstanding toe abutment 20 which has a central, downwardly extending projection 21. This projection 21 projects downwardly through a linear slot 22 in the foot support plate 15 which slot 22 extends in a linear, longitudinal direction towards the middle of the heel abutment 18. The slot 22 acts as a guide for the projection 21 such that the toe abutment 20 can move towards and away from the heel abutment 18. The toe abutment 20 has oppositely disposed rearward facing surfaces 23 which remain generally parallel to the heel abutment 18 when the toe abutment 20 moves towards or away from the heel abutment 18.

Below the foot support plate 15 is a support tray 24 for slidably receiving the TCD 12, the support tray 24 having an open front 25. The tray 24 has a base 26 which is generally parallel to the foot support plate 15, and which is connected to the underside of the foot support plate 15 by means of side connection walls 27. The lateral distance between the side connection walls 27 is ideally matched to the width of the TCD 12 so that the TCD is positioned for accurate sliding in and out through the open front 25 of the support tray 24.

The downward projection 21 of the toe abutment 20 projects into the tray at 28 and can be engaged by the rear facing wall 29 of the TCD 12 when it is inserted into the support tray 24.

At the forward end of the foot support plate there is a movable pointer button 30 which is biased upwardly away from the TCD 12 when inserted in the tray 24. The pointer 30 has a lowermost contact point 31 which, when the pointer 30 is pressed downwardly against the biasing force, engages the touchscreen 32 of the TCD 12. In the embodiment shown, the biasing action is by means of a small coil spring 33 but other biasing mechanisms would be suitable.

The moveable pointer/button 30 is mounted on a forward section 34 which is raised from the foot support plate 15. This forward section also acts as an abutment which limits the possible forward movement of the toe abutment 20. Although not shown, the toe abutment 20 is resiliently biased towards the forward section 34, that is away from the heel abutment. This position is clearly shown in FIG. 1. The biasing action of the toe abutment can easily be achieved by means of springs or other suitable devices/mechanisms.

The abutment of the toe abutment 20 with the forward section 34 effectively sets a datum with regard to the foot measuring process in that the distance between the toe and heel abutments is known.

Figure 2:
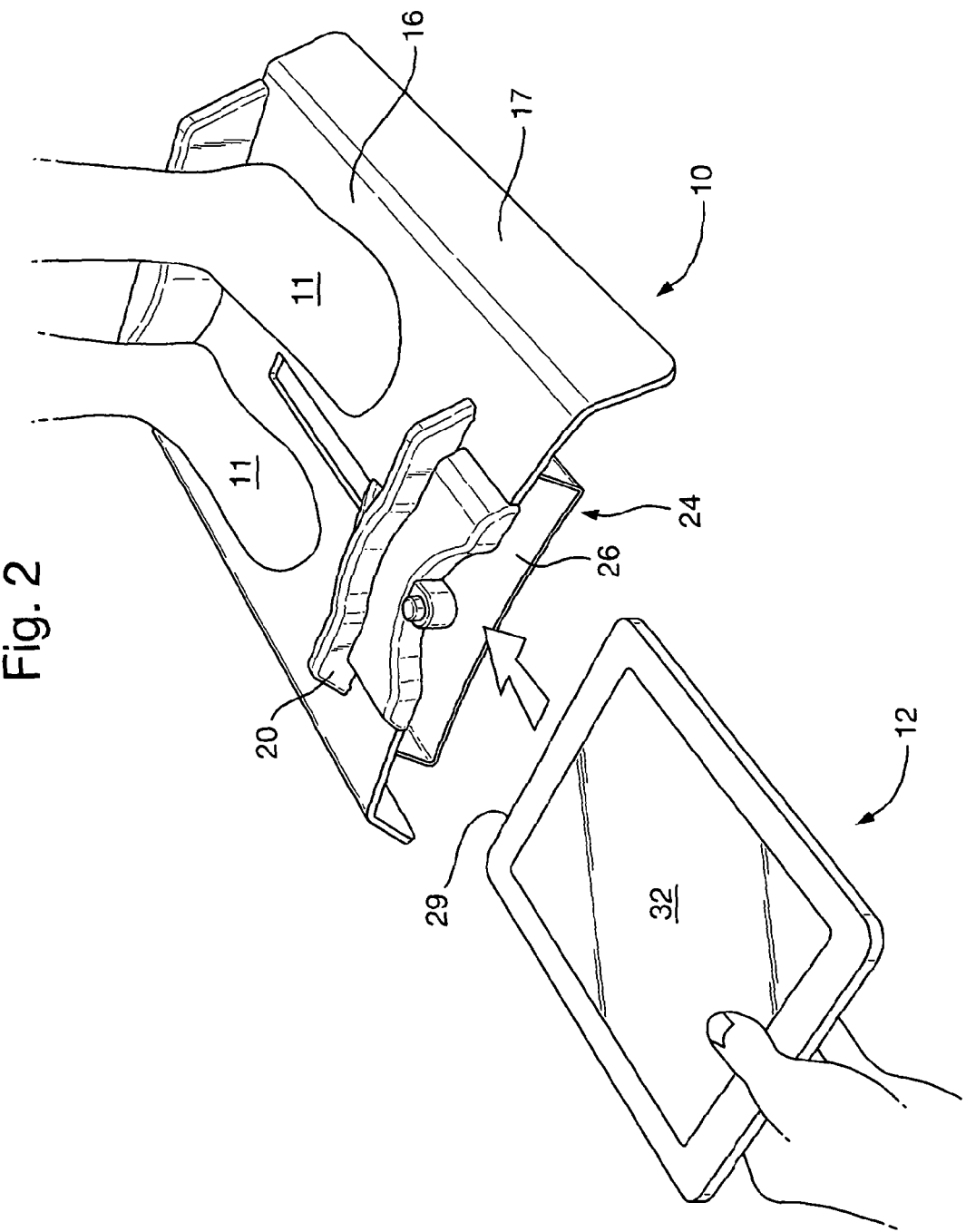
FIG. 2 is a perspective view of the footgauge arrangement of FIG. 1 being used.
Figure 3:
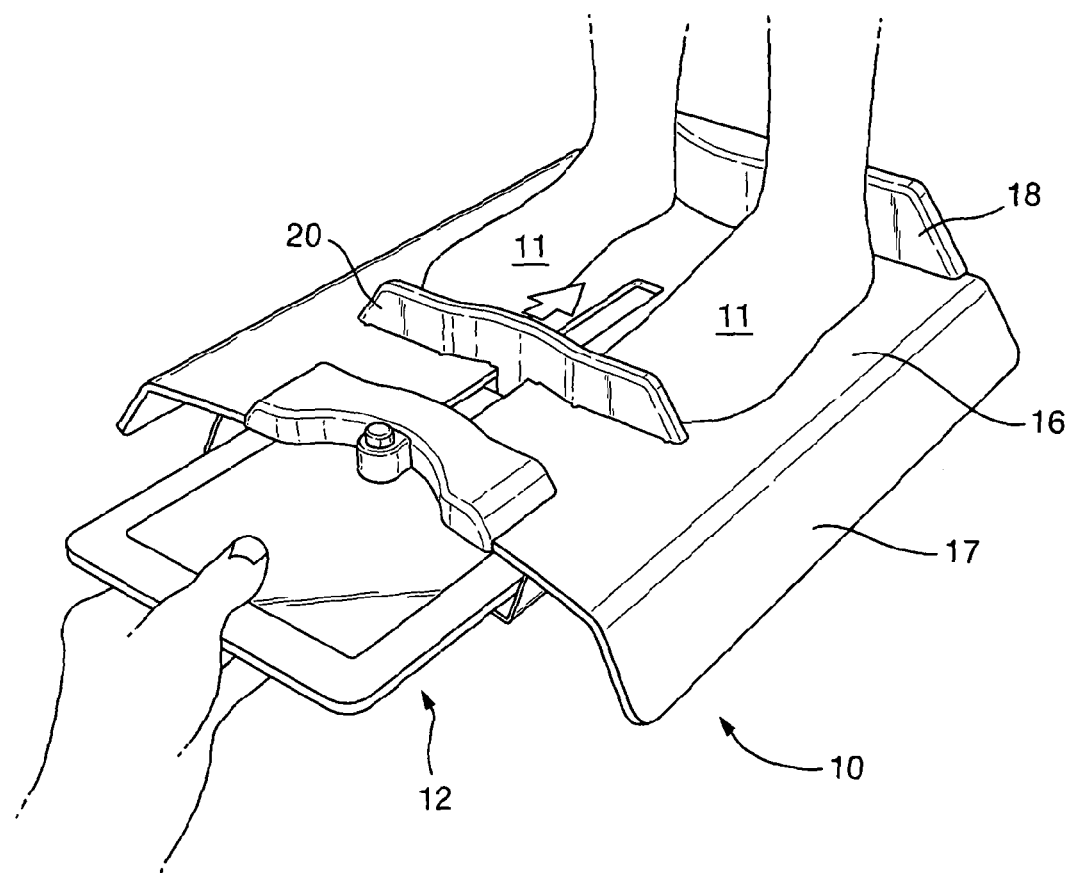
FIG. 3 is a perspective view of the footgauge arrangement of FIG. 1 in a later stage of use.

The use of the footgauge arrangement is shown clearly in FIGS. 2 to 5. The feet 11 to be measured are placed on the upper surface 16 of the foot support plate 15, preferably with the person standing on the footgauge 10. The rear of each foot 11 is placed against the forward facing surface 19 of the heel abutment 18 with the feet 11 on either side of the liner slot 22. This position is shown in FIG. 2 with the TCD 12 about to be inserted into its support tray 24 through its open front 25.

The TCD 12 is slidably moved in a rearward, longitudinal direction until its rear facing wall 29 engages the part 28 of the downward projection 21 of the toe abutment 20. The TCD 12 is moved further in said rearward, longitudinal direction and this causes the toe abutment 20 to move rearwardly towards the heel abutment 18 until the rearward facing surfaces 23 engage the forwardmost point or points of the feet 11. Ideally (but not essentially), the weight of the TCD 12 and friction with the support tray 24 are sufficient to overcome the biasing force which acts to return the toe abutment 20 into its forwardmost position such that the toe abutment 20 remains in position against the feet 11 without manual assistance.

Figure 4:
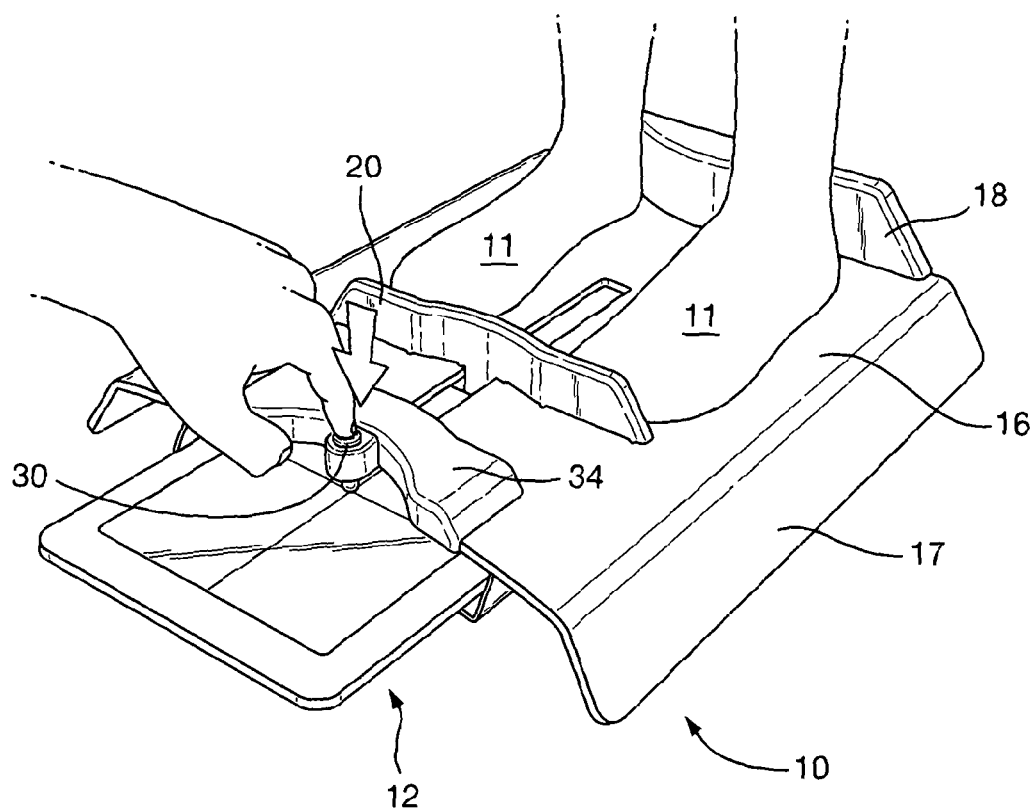
FIG. 4 is a perspective view of the footgauge arrangement of FIG. 1 in a still later stage of use.
Figure 7:
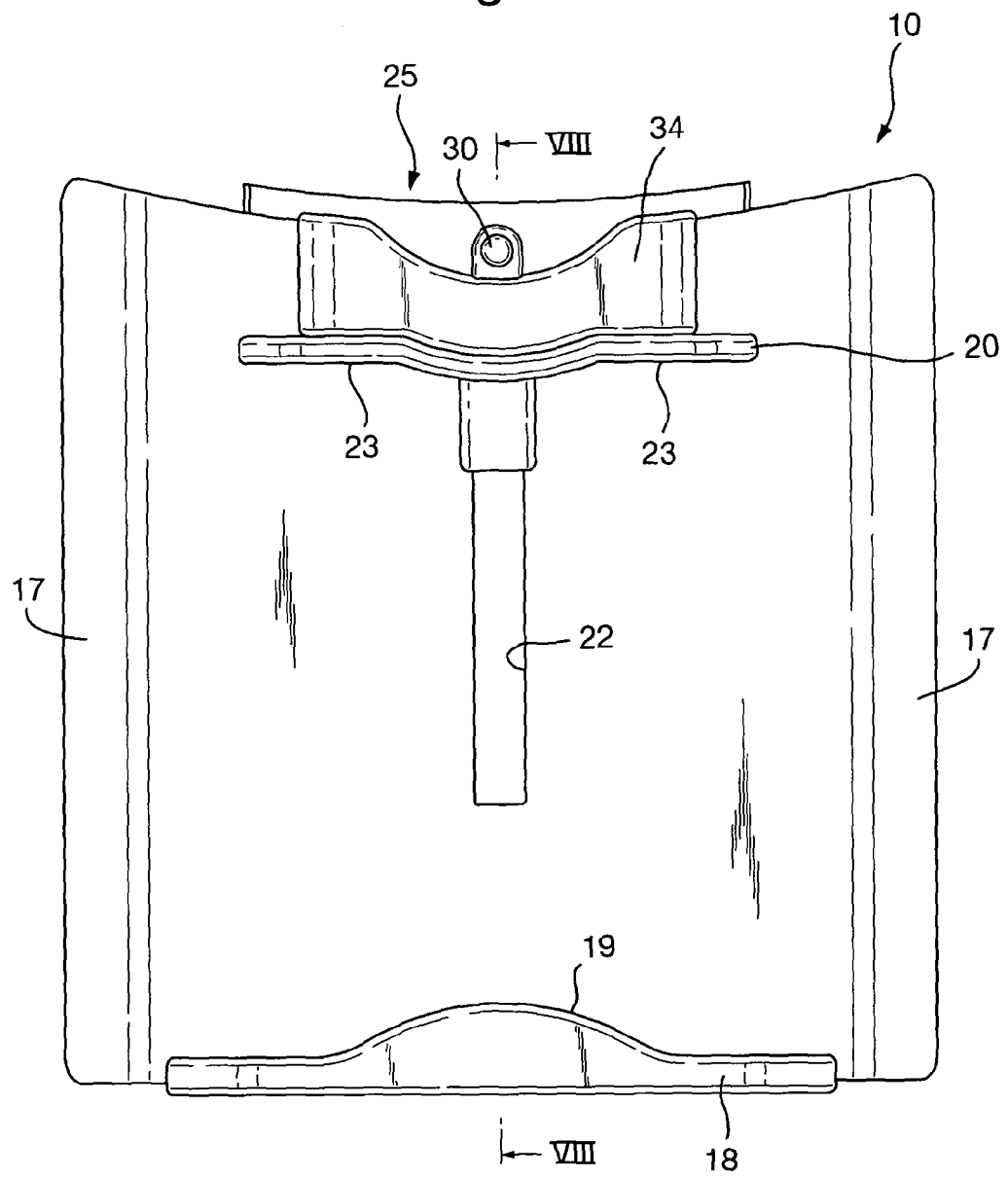
FIG. 7 is a plan view of the footgauge shown in FIG. 1.

Once the toe abutment 20 is in contact with the feet 11, the movable pointer/button 30 can be pressed against the force of the spring 33 such that the lowermost contact point 31 engages the screen 32 of the TCD 12 so as to register a suitable activating contact therewith, as shown in FIG. 4. The pointer/button 30 is then released to return to its rest position.

FIG. 5 gives a simple illustration of the TCD 12 indicating the correct size of the feet 11. Once the size has been registered, the TCD 12 can be removed from its support tray 24 and the toe abutment 20 returns to its forwardmost position by means of the stated biasing action.

The TCD 12 is adapted to incorporate a real-size foot measuring scale programme on its touchscreen 32 so as to display (on activation of the pointer/button 30) a certain, largest size when the TCD 12 abuts the downward projection 21 when the toe abutment 20 is at its forwardmost location against the fixed forward section 34 of the foot support plate 15 because the maximum distance between the heel and toe abutments is known. When the TCD 12 is inserted further and the toe abutment 20 moves rearwardly, the location of the pointer/button 30 effectively moves relative to the scale on the touchscreen 32 of the TCD 12, indicative of a different, i.e. smaller, shoe size which is displayed when the pointer/button 30 is pressed against the screen 32.

The TCD 12 can be linked to a stock control system (not shown) so that the sales assistant will immediately know what particular styles of footwear are in stock for the particular footsize measured. The stock control system can also incorporate images of the styles so that the customer can select those which are of interest so that they can be tried on. The TCD 12 may incorporate this stock control system or it can communicate, ideally via a wireless network, with a central computer which hosts the stock control system.

With some footwear ranges, the width or girth of the feet 11 can also be measured separately and this information can be inputted via a suitable programme shown on the touchscreen. This additional measurement enables a better fit for the footwear, especially children's footwear, but of course may have an effect on stock availability.

The stock control system could also be operative to enable out of stock footwear to be ordered for later delivery to a store or for delivery to the customer's home. Other modifications can, of course, be linked to the TCD 12 which was originally used to measure the foot size of the customer.

The above described footgauge arrangement has a fixed heel abutment and a fixed pointer, with the toe abutment and the TCD being movable together in order to measure the foot. However, it will be readily appreciated that other alternatives are possible. For example, the heel abutment and the TCD could be in fixed locations with the toe abutment, incorporating the pointer, being movable towards and away from the heel abutment. In further alternatives, the heel and toe abutments could be movable with the pointer fixed to one of them and the TCD moving with the other.

In the above described arrangement, the pointer 30 is provided on the forward section 34 which has a fixed location relative to the foot support plate 15. The range of foot lengths which can be measured is somewhat dependent on the length of the TCD screen 32. In the arrangement shown in FIGS. 11 to 14, the forward section 34 is not permanently fixed to the foot support plate 15 but is movable in the lengthwise direction between two set locations defined by the cooperating pairs of holes 60, 61 in the foot support plate 15. One pair of holes 60 is located nearer the heel abutment 18 than the other pair 61. The forward section 34 can be moved between the two positions and fixed in one of the two positions against movement in the lengthwise direction. The toe abutment 20 is still movable away from the forward section 34 towards the heel abutment 18 when urged by the TCD and is again resiliently biased forwards into abutment with the forward section when the TCD is removed.

The two positions (or more if desired) of the forward section enable different datum points for measuring foot length, perhaps for children and for adults. The choices of position can be incorporated into the program or 'app' loaded onto the TCD, with the user inputting which of the two forward section positions has been used so as to ensure correct size information is provided when the pointer is pressed.

Figure 11:
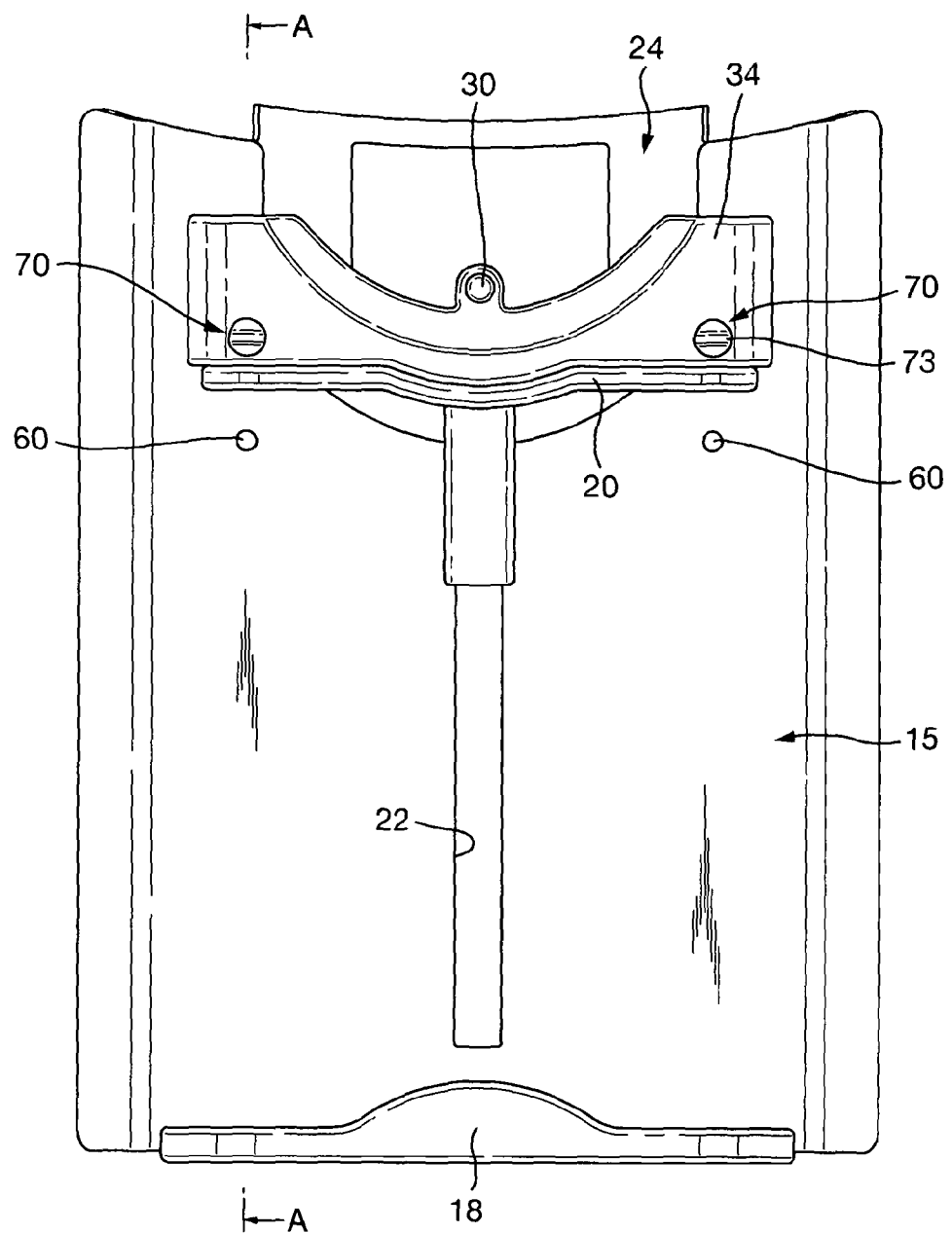
FIG. 11 is a plan view of an alternative footgauge arrangement according to the present invention.
Figure 13:
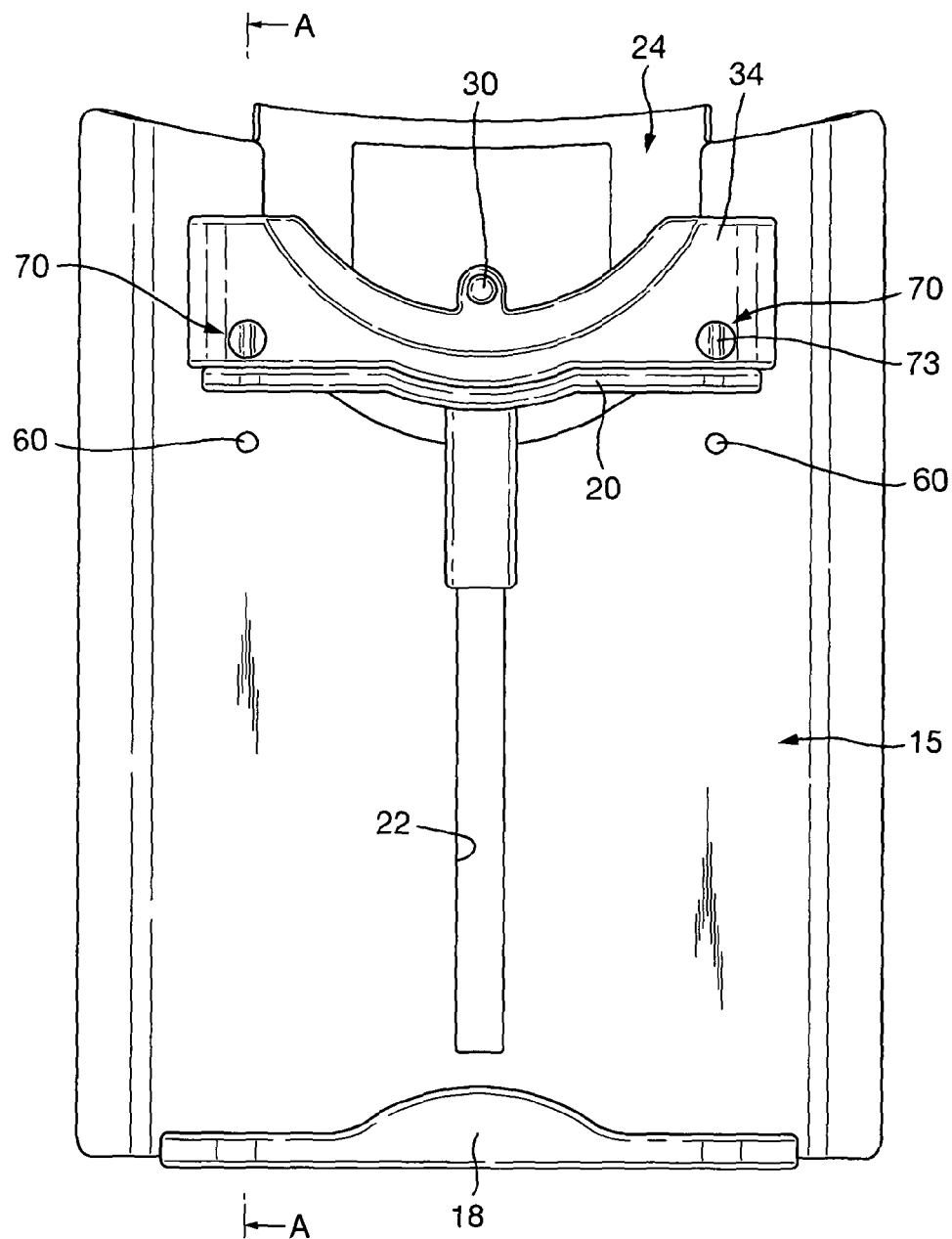
FIG. 13 is a plan view of the FIG. 11 arrangement in a different configuration.
Figure 15:
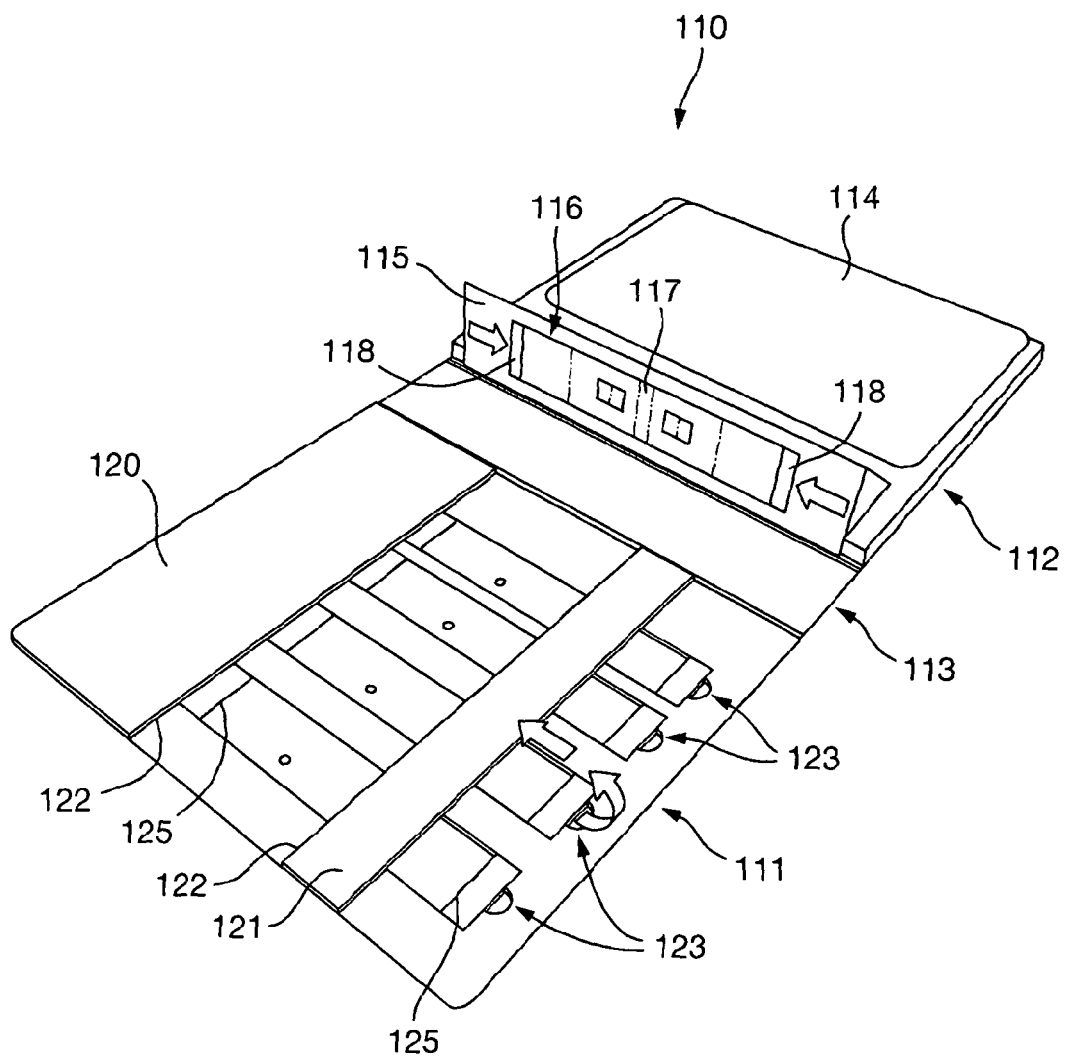
FIG. 15 is a perspective view of an alternative footgauge arrangement according to the present invention being assembled.
Figure 16:
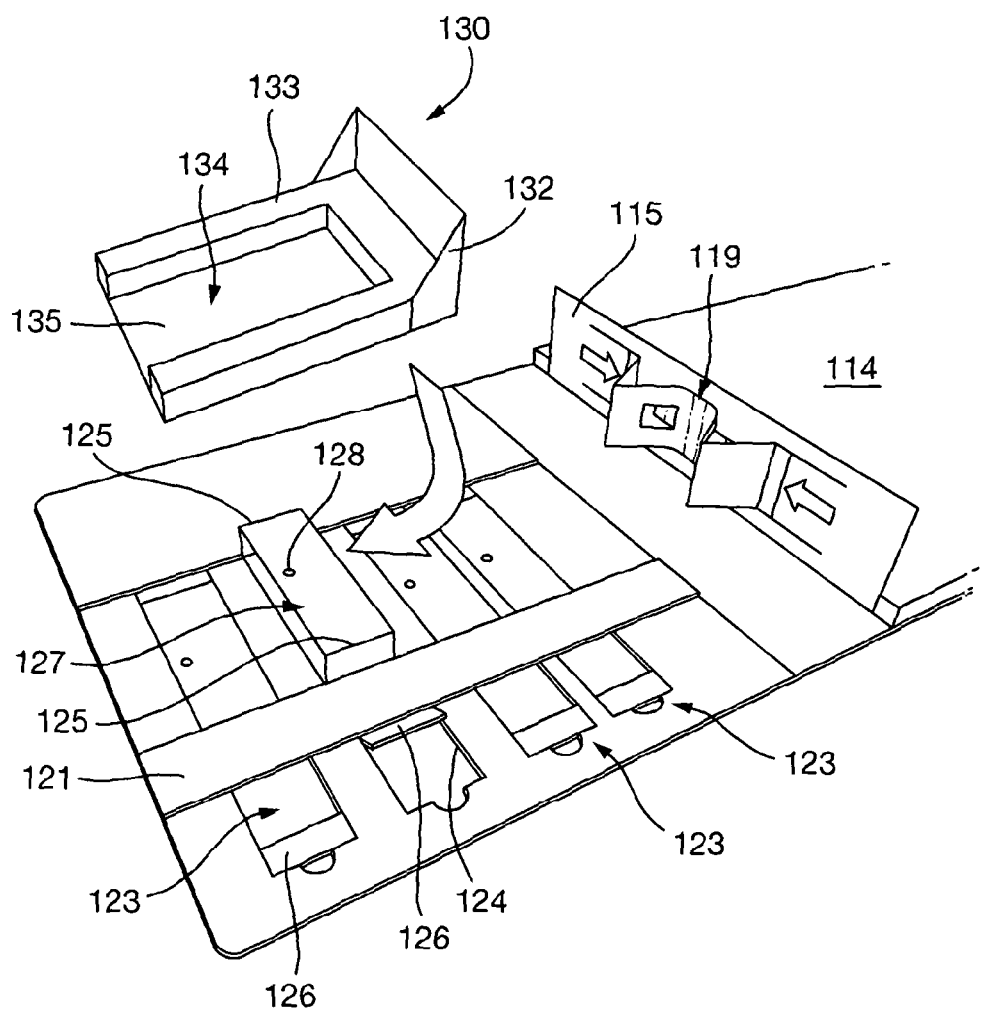
FIG. 16 is a perspective view similar to FIG. 15 in a later stage of assembly.

In the particular arrangement illustrated, the forward section 34 is mounted for sliding movement in the lengthways direction of the footgauge and on each side is provided with a rotatable button 70. Each button 70 is spring loaded in an upward direction by means of a captured coil spring 71 and each button 70 has a lowermost projection 72 and an upper grip flange 73. A known bayonet mechanism (not shown) enables each button 70 to rotate through a quarter turn with a push down and twist operation which moves and retains the projection 72 into raised or lowered positions. The projections 72 can only take up their lowered positions when aligned with one of the pairs of holes 60, 61 in the support plate 15 (FIGS. 11 and 12). When the projections 72 are raised, then the forward section 34 can slide so as to align the projections 72 with one pair of the holes 60, 61 (FIGS. 13 and 14). When the projections 72 are engaged in the holes, the forward section is effectively fixed with respect to the foot support plate and the toe abutment 20 can then be moved away from the forward section 34 to measure the feet in the manner described above in connection with FIGS. 1 to 10.

It will be appreciated that more than two locations can be provided for the forward section 34 combined with suitable program modification for the TCD. Also, the mechanism for locating the forward section 34 against movement relative to the foot support plate 15 in use is just an example of a suitable mechanism.

In FIGS. 15 to 19 there is shown an alternative footgauge 110 for use in measuring feet. Ideally, the footgauge 110 is folded from paperboard or another sheet material having sufficient rigidity for the purpose. Conveniently, the footgauge 110 is intended for home use rather than in-store use, the consumer either collecting the footgauge 110 as a flat-pack in store or receiving the flat-pack by post/courier. In some embodiments, and as illustrated in FIGS. 15 to 19 the footgauge 110 is similar in form to a file having front and rear covers 111, 112 linked by folds to a central spine 113.

The rear cover 112 may incorporate instructions 114 and/or a sheet for recording the growth of a child's foot. Upstanding from the fold junction of the rear cover 112 and the central spine 113 is a wall 115 which is perpendicular to the floor when the footgauge file is folded out as shown in the figures. One or more fold-up reinforcement panels may be provided behind the wall 115 so that the wall can be braced in its upright position relative to the spine 113 in use. The height of the wall 115 is less than the width of the spine so that when the footgauge file is closed the wall 115 does not interfere with the front cover 111. The wall incorporates a length of paperboard 116 which is fixed at a central location 117. The ends 118 of the length of paperboard 116 slide inwardly towards the central location and lock in place using suitable interlocking formations (not shown) so as to provide a generally C-shaped (in plan view) heel abutment 119 for receiving the rear of the foot to be measured.

Forwardly of the heel abutment 119, the front cover 111, which effectively constitutes a foot support plate, incorporates two pieces of board 120, 121 which are slightly upstanding so as to constitute a pair of parallel guide rails 122 which are perpendicular to the fold between the front cover 111 and the spine 113. A series of paperboard bridge members 123 are provided in channels 124 in the front cover 111. Each bridge member 123 has one end secured beneath the first piece of board 120 but is slidably located beneath the second piece of board 121. Each bridge member 123 has a series of transverse folds 125 and a finger tab 126 remote from its fixed end. Each bridge member 123 can be manipulated by a sliding/lifting action so as to form a rectangular bridge 127 over the surface between the guide rails 122. This is shown clearly in FIG. 16. In use, only one bridge member 123 is to be raised at a time, depending on the length of the foot being measured, the bridge members 123 being provided at increasing distances from the heel abutment 119. Each bridge member has a central hole 128 and the purpose of this will be discussed later.

A support block 130 is provided for receiving a touch-screen computer device (TCD) 131. In this particular embodiment the TCD 131 is in the form of a smart phone having a touchscreen 136. The support block 130 can be folded from a flat sheet of paperboard and provides a toe abutment 132 and a box section tray 133 with a central depression 134 and floor 135 for receiving snugly the TCD. The size of the depression may be changeable by means of folds or shaped inserts for example so as to accommodate a variety of sizes of TCD. Generally the height of the box section tray 133 is slightly greater than the thickness of the TCD and is about the same as the height of each bridge 127. The width of the box section enables it to be slidably received between the guide rails 122 for guided movement towards and away from the heel abutment 119.

Figure 17:
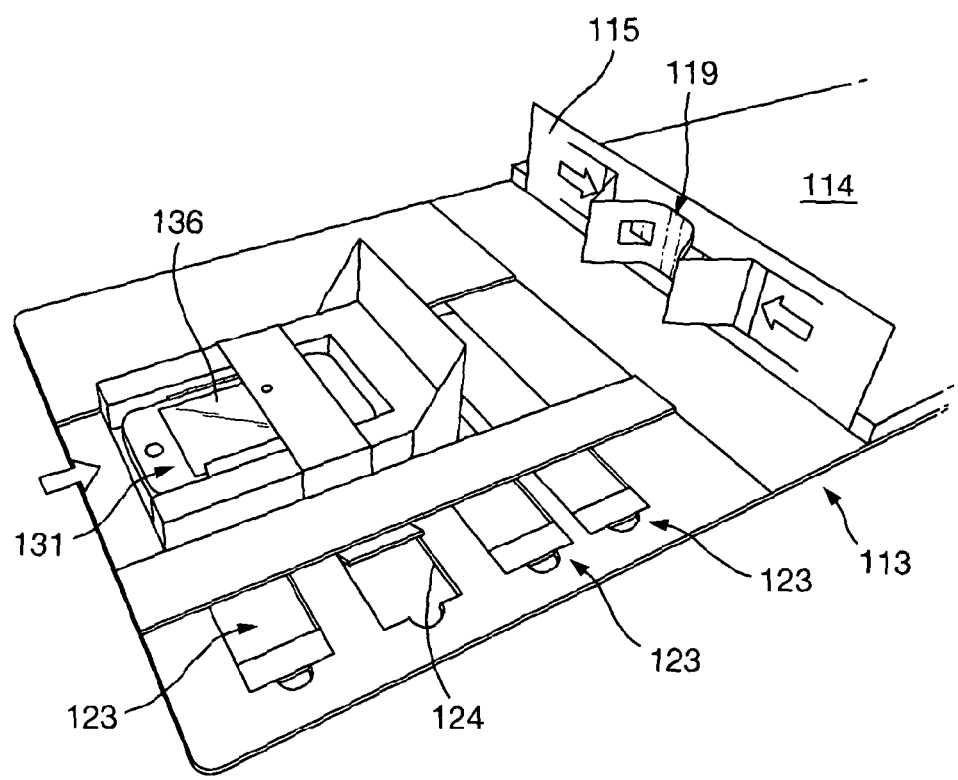
FIG. 17 is a perspective view similar to FIG. 16 in a later stage of assembly.

With one of the bridges 127 raised, as shown in FIG. 17, the box section tray 133 can be slidably inserted below the bridge 127, the sliding action towards and away from the heel abutment being guided by the parallel guide rails 122. The TCD is then inserted into its position in the tray 133 such that the screen 136 of the TCD moves longitudinally beneath the hole 128 of the bridge.

Figure 18:
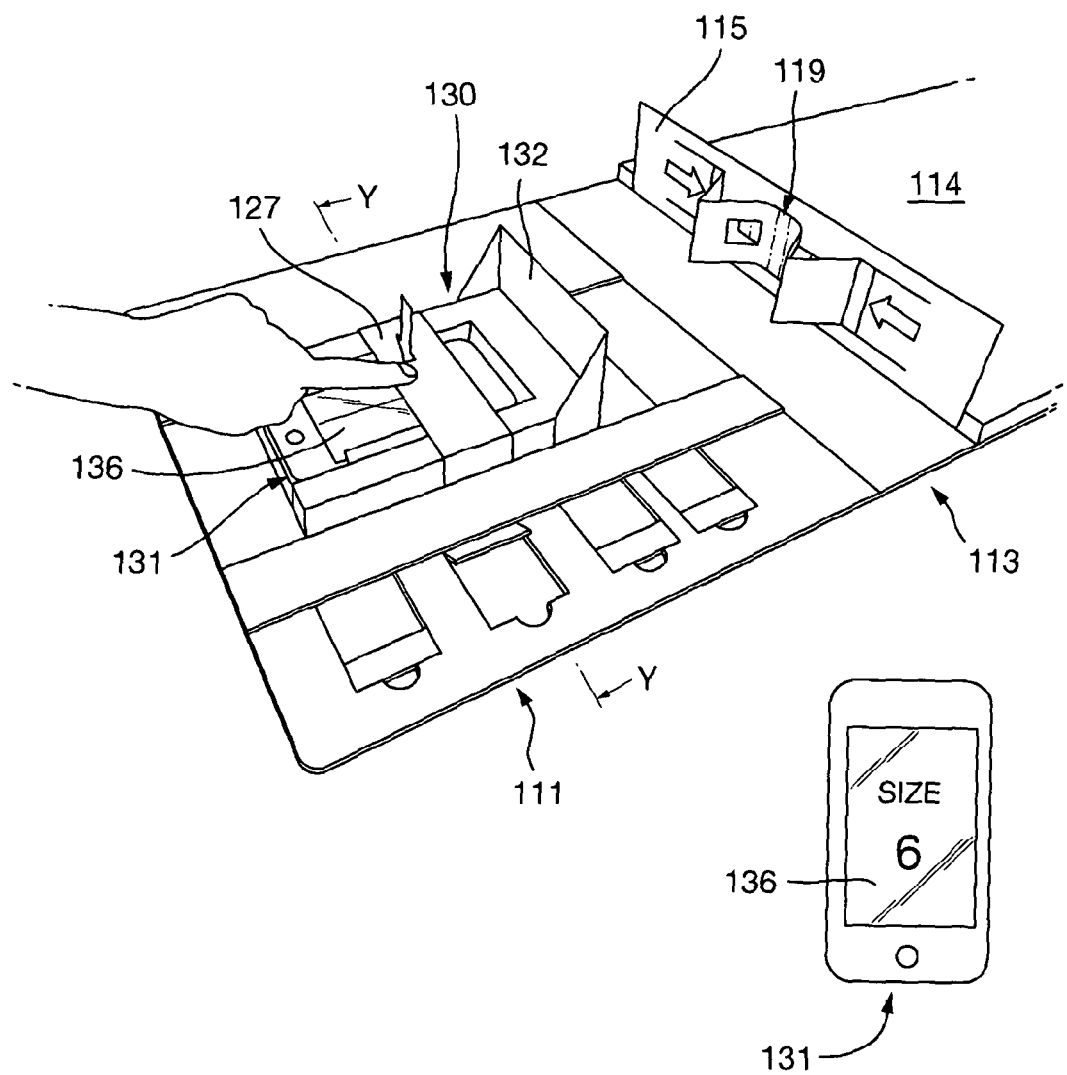
FIG. 18 is a perspective view similar to FIG. 17 of the alternative footgauge in use but omitting the foot being measured.
Figure 19A:
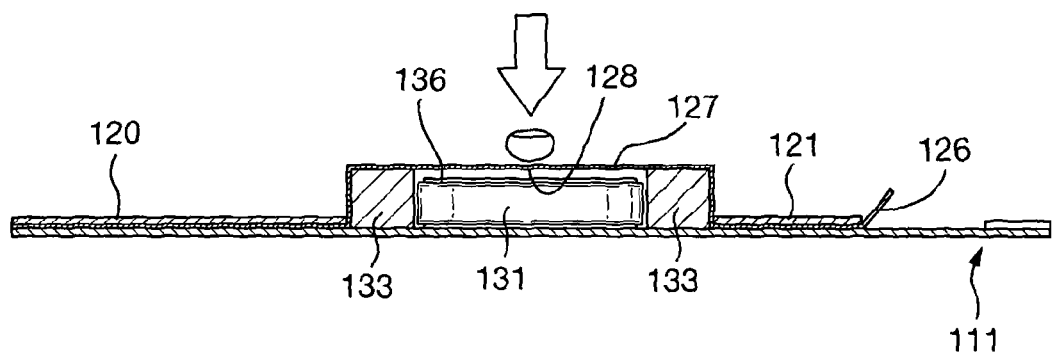
FIGS. 19a and 19b are lateral cross-sections on line Y-Y showing the measuring taking place.
Figure 19B:
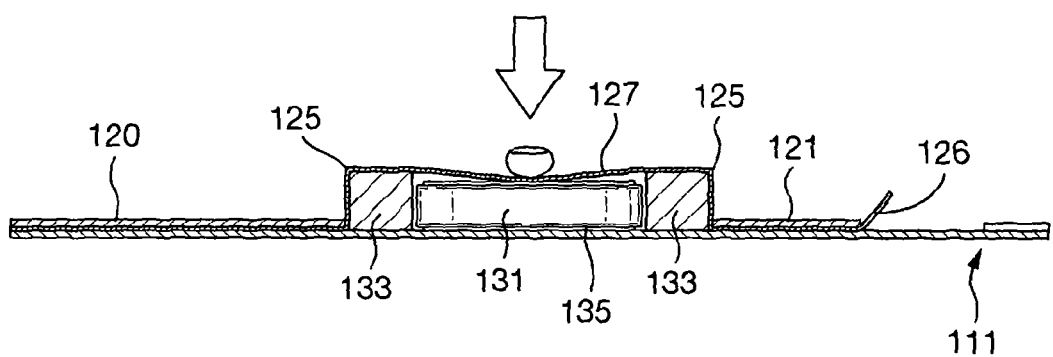

FIG. 18 shows the footgauge 110 in use although no foot is shown. The foot to be measured is placed on the footgauge 110 with the heel of the foot against the heel abutment 119. The foot measurement should be made with the user's weight on the foot with the footgauge 110 ideally opened out on to the floor. Each bridge member 123 is associated with a range of overlapping foot sizes so the appropriate bridge member 123 is raised according to a rough estimate, perhaps indicated in the instructions 114. The support block 130 with the TCD is then moved towards the foot until the endmost toe is engaged by the toe abutment 132. The measurer then places a finger over the hole 128 and flexes the bridge 127 downwardly so as to contact the screen 136 of the TCD. The TCD 131 then gives a foot length indication on the screen.

The TCD 131 incorporates a program or 'app' that effectively measures the distance from the hole 128 to the toe abutment and this is coupled to the known distance from the hole 128 to the heel abutment 119. All the user needs to do is to input which bridge member 123 is being used so that the correct hole 128/heel abutment 119 distance is used in the calculation. The other TCD features discussed above in relation to the first embodiment of FIGS. 1 to 10 are equally applicable to the alternative embodiments. Similarly, the TCD 131 need not be a phone but could also be a larger, 'tablet' type device having a touchscreen.

It will also be appreciated that the precise design and materials of manufacture of the footgauge can be modified whilst remaining within the scope of the accompanying claims.

The invention claimed is:

1. A footgauge for measuring the length of a foot, the footgauge comprising:
   (i) a foot support having a foot support plate on which the underside of the foot is placed;
   (ii) a heel abutment for engaging the heel of the foot;
   (iii) a toe abutment for engaging the foremost extremity of the foot;
   (iv) a support for receiving a touchscreen computer device;
   (v) a pointer element configured to provide engagement with the touchscreen computer device to indicate the length of the foot, wherein the pointer element is provided in a fixed location relative to the foot support plate;
   wherein one or both of the heel abutment and the toe abutment are movable relative to each other.

2. The footgauge as claimed in claim 1, wherein the heel abutment is fixed relative to the foot support and the toe abutment is movable in a linear lengthwise direction towards or away from the heel abutment.

3. The footgauge as claimed in claim 2, wherein the toe abutment has a downward projection which projects through a guide slot in the foot support plate, the guide slot extending in said linear lengthwise direction.

4. The footgauge as claimed in claim 2, wherein the support comprises a support block attached to, and forwardly of, the toe abutment for sliding movement on said foot support plate beneath said contact means.

5. The footgauge as claimed in claim 4 wherein the support block has parallel side walls for guided movement towards and away from the heel abutment between two side guide rails.

6. The footgauge as claimed in claim 4 wherein the heel abutment is provided on a wall which is attached to the foot support plate and is retainable in a position perpendicular to the foot support plate.

7. The footgauge as claimed in claim 6 wherein the heel abutment folds out of the wall to provide a heel locating structure.

8. A footgauge for measuring the length of a foot, the footgauge comprising:
   a foot support having a foot support plate on which the underside of the foot is placed;
   a heel abutment for engaging the heel of the foot;
   a toe abutment for engaging the foremost extremity of the foot;
   a support for receiving a touchscreen computer device;
   a movable contact having a contact point; and
   a touchscreen computer device located on a support tray located below the foot support plate, the width of the support tray enabling the touchscreen computer device to be slidably moved in a linear lengthwise direction with the plane of the screen being parallel with the general plane of the foot support plate and the support tray being open at its forward end for receiving the touchscreen computer device, and the contact point of the movable contact being positioned to contact a touchscreen surface of the touchscreen computer device, the touchscreen computer device being programmed to give a foot length indication when the screen is contacted by the contact point of the movable contact;
   wherein one or both of the heel abutment and the toe abutment are movable relative to each other,
   wherein the heel abutment is fixed relative to the foot support and the toe abutment is movable in a linear lengthwise direction towards or away from the heel abutment, and
   wherein the toe abutment has a downward projection which projects through a guide slot in the foot support plate, the guide slot extending in said linear lengthwise direction.

9. The footgauge as claimed in claim 8, wherein the downward projection of the toe abutment extends downwardly into the support tray so as to be engaged in use by the rear end of the touchscreen computer device, rearward movement of the touchscreen computer device moving the toe abutment rearwardly into engagement with the foot.

10. The footgauge as claimed in claim 8, wherein said contact comprises a movable pointer which is provided in a fixed location relative to the foot support and which is resiliently biased away from the touchscreen computer device when in use but is selectively movable into engagement with the screen of the touchscreen computer device.

11. The footgauge as claimed in claim 10 wherein the pointer is provided on a forward section which is movable between, and securable in, a number of fixed locations relative to the foot support.

12. The footgauge as claimed in claim 11 wherein the forward section is securable by means of one or more buttons having a push down/twist bayonet mechanism engaging in cooperating holes in the foot support.

13. The footgauge as claimed in claim 8, wherein the touchscreen computer device is programmed to indicate footwear availability for each foot length indication.

14. A footgauge for measuring the length of a foot, the footgauge comprising:
   a foot support having a foot support plate on which the underside of the foot is placed;
   a heel abutment for engaging the heel of the foot;
   a toe abutment for engaging the foremost extremity of the foot;
   a support for receiving a touchscreen computer device; and
   a movable contact having a contact point,
   wherein the heel abutment is fixed relative to the foot support and the toe abutment is movable in a linear lengthwise direction towards or away from the heel abutment,
   wherein the support comprises a support block attached to, and forwardly of, the toe abutment for sliding movement on said foot support plate beneath said contact means, wherein the support block has parallel side walls for guided movement towards and away from the heel abutment between two side guide rails, and wherein said movable contact comprises a bridge which spans the two side rails and which has a hole therethrough.

15. The footgauge as claimed in claim 14 wherein the bridge is foldable into the plane of the foot support plate.

16. The footgauge as claimed in claim 15 wherein a number of foldable bridges are provided at spaced intervals forward of the heel abutment, one bridge being raised for cooperation with the support block depending on foot length.

17. The footguage as claimed in claim 14, further comprising a touchscreen computer device located on the support block, the touchscreen computer device being programmed to give a foot length indication when the screen is contacted through the hole in the bridge.

18. The footgauge as claimed in claim 17, wherein the touchscreen computer device is programmed to indicate footwear availability for each foot length indication.

19. A footgauge for measuring the length of a foot, the footgauge comprising:
 (i) a foot support having a foot support plate on which the underside of the foot is placed;
 (ii) a heel abutment for engaging the heel of the foot;
 (iii) a toe abutment for engaging the foremost extremity of the foot;
 (iv) a support for receiving a touchscreen computer device, wherein the touch screen device is configured to engage a pointer to indicate the length of the foot, wherein the pointer is provided in a fixed location relative to the foot support plate, and wherein one or both of the heel abutment and the toe abutment are movable relative to each other.

\* \* \* \* \*